US012496413B2

(12) United States Patent
Zuber et al.

(10) Patent No.: US 12,496,413 B2
(45) Date of Patent: Dec. 16, 2025

(54) DRY POWDER INHALER

(71) Applicant: PHILIP MORRIS PRODUCTS S.A., Neuchâtel (CH)

(72) Inventors: Gerard Zuber, Boulens (CH); Christopher Grant, Neuchâtel (CH); Daniele Sanna, Marin-Epagnier (CH); Gianluca Sechi, Colombier (CH); Judith Waller, Ostersund (SE); Niki Meloncelli, Castel Maggiore (IT)

(73) Assignee: Philip Morris Products S.A., Neuchâtel (CH)

( * ) Notice: Subject to any disclaimer, the term of this patent is extended or adjusted under 35 U.S.C. 154(b) by 1520 days.

(21) Appl. No.: 16/970,846

(22) PCT Filed: Feb. 15, 2019

(86) PCT No.: PCT/IB2019/051239
§ 371 (c)(1),
(2) Date: Aug. 18, 2020

(87) PCT Pub. No.: WO2019/159123
PCT Pub. Date: Aug. 22, 2019

(65) Prior Publication Data

US 2021/0113787 A1 Apr. 22, 2021

(30) Foreign Application Priority Data

Feb. 19, 2018 (EP) .................................... 18157483

(51) Int. Cl.
*A61M 15/00* (2006.01)
*A24F 42/20* (2020.01)
(Continued)

(52) U.S. Cl.
CPC ......... *A61M 15/0005* (2014.02); *A24F 42/20* (2020.01); *A24F 42/60* (2020.01);
(Continued)

(58) Field of Classification Search
CPC ............ A61M 15/008; A61M 15/0021; A61M 15/0035; A61M 15/06; A61M 2202/064;
(Continued)

(56) References Cited

U.S. PATENT DOCUMENTS 2,573,918 A * 11/1951 McCuiston ........... B05B 11/062 604/60
4,069,819 A * 1/1978 Valentini ........... A61M 15/0033 604/131
(Continued)

FOREIGN PATENT DOCUMENTS

RU 2424000 7/2011
WO 20170109626 6/2017
(Continued)

OTHER PUBLICATIONS

European Search Report for EP Application No. 18157483.1 issued by the European Patent Office on Aug. 13, 2018; 8 pgs.
(Continued)

*Primary Examiner* — Justine R Yu
*Assistant Examiner* — Gwynneth L Howell
(74) *Attorney, Agent, or Firm* — Mueting Raasch Group

(57) ABSTRACT

A dry powder inhaler for providing pharmaceutically active particles includes a mouthpiece portion removably coupled to a distal end portion. The mouthpiece portion extends between the mouthpiece end and a first mating end. The distal end portion extends between a second mating end and the distal end. A capsule cavity is defined within the first mating end. An airflow element is disposed within the distal end portion and extends a longitudinal length to the capsule cavity. The airflow element includes an airflow channel extending the longitudinal length of the airflow channel and non-parallel with the longitudinal axis, the airflow channel directs inlet air into the capsule cavity, and a resealable
(Continued)

membrane configured to reseal when a piercing element is withdrawn from the resealable membrane.

20 Claims, 3 Drawing Sheets

(51) Int. Cl.
*A24F 42/60* (2020.01)
*A61M 15/06* (2006.01)

(52) U.S. Cl.
CPC ...... *A61M 15/0008* (2014.02); *A61M 15/002* (2014.02); *A61M 15/0021* (2014.02); *A61M 15/0028* (2013.01); *A61M 15/003* (2014.02); *A61M 15/0033* (2014.02); *A61M 15/0035* (2014.02); *A61M 15/0041* (2014.02); *A61M 15/06* (2013.01); *A61M 2202/064* (2013.01); *A61M 2206/16* (2013.01)

(58) Field of Classification Search
CPC .............. A61M 2206/16; A61M 15/00; A61M 15/0005–0008; A61M 15/002; A61M 15/003; A61M 15/0033; A61M 15/0041; A61M 2201/0007; A61M 2205/0216; A61M 2205/076; A61M 2210/0625; A61M 15/036; A24F 42/20; A24F 42/60; A24F 40/05; A24F 40/20
USPC .......................... 128/203.21, 203.12, 203.15
See application file for complete search history.

(56) References Cited

U.S. PATENT DOCUMENTS

| | | | | | |
|---|---|---|---|---|---|
| 4,116,195 | A * | 9/1978 | James | A61M 15/0033 | 222/83.5 |
| 7,837,657 | B2 * | 11/2010 | Mazidji | A61M 5/3287 | 604/218 |
| 8,539,946 | B2 | 9/2013 | Esteve et al. | | |
| 8,746,244 | B2 * | 6/2014 | Kaemper | A61M 15/0028 | 128/203.23 |
| 10,124,128 | B2 * | 11/2018 | Burr | A61M 15/003 | |
| 2003/0094173 | A1 * | 5/2003 | Burr | A61M 15/0028 | 222/394 |
| 2003/0131847 | A1 * | 7/2003 | Niccolai | A61M 15/0028 | 128/203.15 |
| 2004/0173211 | A1 * | 9/2004 | Kladders | A61M 15/0048 | 128/203.15 |
| 2005/0022813 | A1 * | 2/2005 | Alston | A61M 15/0041 | 128/203.15 |
| 2008/0251072 | A1 * | 10/2008 | Lulla | A61M 11/002 | 128/203.15 |
| 2010/0006096 | A1 * | 1/2010 | Kakade | A61M 15/0065 | 128/203.15 |
| 2011/0048414 | A1 * | 3/2011 | Hoekman | A61M 31/00 | 128/200.23 |
| 2011/0277752 | A1 * | 11/2011 | Cheu | A61M 15/0035 | 128/200.14 |
| 2015/0020822 | A1 * | 1/2015 | Janardhan | A61M 15/06 | 131/328 |
| 2018/0140789 | A1 * | 5/2018 | Pieters | A61M 15/0028 | |
| 2018/0147371 | A1 * | 5/2018 | Stenzler | A61M 15/06 | |
| 2019/0083720 | A1 * | 3/2019 | Leadley | A24F 40/485 | |

FOREIGN PATENT DOCUMENTS

| | | | | |
|---|---|---|---|---|
| WO | WO-2017109678 | A1 * | 6/2017 | A24B 15/186 |
| WO | WO-2018007887 | A1 * | 1/2018 | A24B 15/16 |
| WO | WO 2018/100461 | A1 | 6/2018 | |

OTHER PUBLICATIONS

International Search Report and Written Opinion for PCT/IB2019/051239, issued by the European Patent Office on May 3, 2019; 16 pgs.
International Preliminary Report on Patentability for PCT/IB2019/051239, issued by the European Patent Office on May 12, 2020; 8 pgs.
Cohen et al., "GRAS Flavoring Substances," 27. *GRAS Flavoring Substances. Food Technology for Flavoring Extract Manufacturers Association*, Aug. 2015:69(8):40-59.
Hall, R.L. & Oser, B.L., "Recent Progress in the Consideration of Flavoring Ingredients under the Food Additive Amendments 3. GRAS substances," *Food Technology*, Feb. 1965: p. 151-197.
Russian Office Action for RU Application No. 2020123697, issued by the Patent Office of the Russian Federation; Jun. 7, 2022; 15 pgs. including English translation.

* cited by examiner

DRY POWDER INHALER

This application is the § 371 U.S. National Stage of International Application No. PCT/IB2019/051239, filed 15 Feb. 2019, which claims the benefit of European Application No. 18157483.1, filed 19 Feb. 2018, the disclosures of which are incorporated by reference herein in their entireties.

This disclosure relates to a dry powder inhaler that provides multi-use delivery of pharmaceutically active particles.

Dry powder inhalers are not typically suitable to provide pharmaceutically active particles to the lungs at inhalation or air flow rates that are within conventional smoking regime inhalation or air flow rates. Dry powder inhalers do not always include dry powder consumable which is easily replaceable once consumed.

It is desirable to provide a dry powder inhaler system that provides multi-use delivery of pharmaceutically active particles. It is desirable that the dry powder inhaler include a modular component capsule receptacle that may be easily replaceable once consumed. It is desirable that the inhaler facilitate delivery of pharmaceutically active particles to the consumer at conventional smoking regime inhalation or air flow rates.

This disclosure is directed to a reusable dry powder inhaler suitable for providing pharmaceutically active particles, preferably including nicotine particles, that includes a mouthpiece portion removably coupled to a distal end portion. The mouthpiece portion includes a capsule cavity and a mouthpiece air channel extending from the mouthpiece end to the capsule cavity. The distal end portion includes an airflow element disposed within the distal end portion and extending a longitudinal length to the capsule cavity. The airflow element includes an airflow channel extending the longitudinal length of the airflow element and is non-parallel with the longitudinal axis. The airflow channel directs inlet air into the capsule cavity and a resealable membrane is configured to reseal when a piercing element is withdrawn from the resealable membrane.

The dry powder inhaler may include an inhaler body extending from a mouthpiece end to a distal end and include a mouthpiece portion removably coupled to a distal end portion. The mouthpiece portion extends between the mouthpiece end and a first mating end. The distal end portion extends between a second mating end and the distal end. The mouthpiece portion includes a capsule cavity defined within the first mating end and a mouthpiece air channel extending from the mouthpiece end to the capsule cavity.

The distal end portion may include a piercing element coupled to the distal end portion and an airflow element disposed within the distal end portion and extending a longitudinal length to the capsule cavity. The piercing element is configured to move between a relaxed position and a piercing position. The piercing element extends through the airflow element and resealable membrane within the airflow element and into the capsule cavity in the piercing position. The resealable membrane is configured to reseal when the piercing element moves from the piercing position to the relaxed position.

The airflow element includes one or more airflow channels that produce swirling air flow to induce rotation of the capsule contained within the capsule cavity. Rotation of the capsule with the swirling air flow may cause the capsule to release pharmaceutically active particles (once pierced) into the airflow. The release may provide a fractional amount of pharmaceutically active particles with each air flow "puff" by the consumer. Each fractional amount of dry powder released may be substantially equal or equivalent to each other. The capsule may be considered a multiple-use element. The capsule may be emptied (or depleted) of dry powder with about 8 to 25 inhalations or "puffs", for example.

Preferably the resealable membrane occludes a linear piercing channel that extends the length of the airflow element. The resealable membrane may prevent air flow into the capsule cavity via the linear piercing element.

The capsule may be a modular component of the multiple-use dry powder inhaler. The capsule may be easily replaceable within the multiple-use inhaler. Once consumed, the capsule may be removed from the multiple-use dry powder inhaler and discarded.

Advantageously, the dry powder inhaler described herein provides a re-usable modular component approach when combined with a consumable capsule. The airflow element within the distal end portion of the inhaler ensures that swirling airflow enters the capsule cavity. The airflow element may be reliably formed with a molding process and easily assembled into the inhaler. This air flow management ensures that the capsule rotates during inhalation and consumption. This rotation may suspend and aerosolize the pharmaceutically active particles in the inhalation air moving through the dry powder inhaler. The pharmaceutically active particles may be delivered with the dry powder inhaler at inhalation or air flow rates that are within conventional smoking regime inhalation or air flow rates.

The dry powder inhaler described herein may provide dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This dry powder inhaler may mimic the ritual of conventional smoking. This dry powder inhaler may be simple to manufacture and convenient to use by a consumer.

Air flow management through the capsule cavity may cause the capsule to rotate during inhalation and consumption. The capsule contains pharmaceutically active particles in a dry powder form. This dry powder may optionally include particles comprising flavour, also referred to as "flavour particles.

A preferred pharmaceutically active particle is nicotine particle. Nicotine particles comprise nicotine and may be referred to as "nicotine powder" or "nicotine particles".

Rotation of the pierced capsule may suspend and aerosolize the pharmaceutically active particles released from the pierced capsule into the inhalation air moving through the dry powder inhaler. The flavour particles may be larger than the pharmaceutically active particles and may assist in transporting the pharmaceutically active particles into the lungs of the user while the flavour particles preferentially remain in the mouth or buccal cavity of the user. The pharmaceutically active particles and optional flavor particles may be delivered with the dry powder inhaler article at inhalation or air flow rates that are within conventional smoking regime inhalation or air flow rates.

The term "pharmaceutically active" particle refers to particles that alters one or more chemical or physiological functions of a cell, tissue, organ, or organism. A pharmaceutically active component of a particle may be, for example, a systemic or local drug, a peptide or DNA based drug, an anti-inflammatory agent, a bronchodilating agent, an antiviral agent, an antibiotic agent, an immunostimulatory agent, an immunosupressive agent, an anesthetic agent, an anticancer agent, a vitamin, a hormone, an antiepileptic agent, an antifungal agent, an antioxidant, an antidiabetic agent, a muscle relaxant, and anti-HIV agent, a stimulant, a cough suppressant, a pain controller, a smoking cessation agent or an alcohol abuse agent. Preferably the pharmaceutically active component of a particle is nicotine.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The size of a particle, stated herein, preferably refers to the aerodynamic diameter of the particle. The aerodynamic diameter of the particles is preferably measured with a cascade impactor.

The dry powder inhaler described herein may be combined with one or more modular pharmaceutically active particle delivery consumables (capsules) to deliver pharmaceutically active particles to a consumer. A plurality of these modular pharmaceutically active particle delivery consumables (similar or different formulation or flavors) may be combined with a dry powder inhaler to form a kit.

The dry powder inhaler described herein may be combined with a piercing element or piercing device to deliver the pharmaceutically active particles to a consumer. The piercing element or piercing device may be separated from or not form a portion of the dry powder inhaler article. A plurality of these dry powder inhaler articles may be combined with a piercing element or piercing device to form a kit.

Alternatively, the dry powder inhaler described herein may include a piercing element or piercing device coupled to the distal end portion.

The dry powder inhaler includes a mouthpiece portion removably coupled to a distal end portion. The mouthpiece portion includes a capsule cavity and a mouthpiece air channel extending from the mouthpiece end to the capsule cavity. The distal end portion includes an airflow element disposed therein. The airflow element includes an airflow channel (or two or more airflow channels) extending the longitudinal length of the airflow element and is non-parallel with the longitudinal axis. The airflow channel directs inlet air into the capsule cavity. The airflow element includes a resealable membrane configured to reseal when a piercing element is withdrawn from the resealable membrane.

The dry powder inhaler body extends from a mouthpiece end to a distal end. The inhaler body includes a mouthpiece portion removably coupled to a distal end portion. The mouthpiece portion extending between the mouthpiece end and a first mating end. The distal end portion extending between a second mating end and the distal end.

The mouthpiece portion includes a capsule cavity defined within the first mating end, and a mouthpiece air channel extending from the mouthpiece end to the capsule cavity.

The distal end portion includes an airflow element disposed within the distal end portion and extends a longitudinal length to the capsule cavity. The airflow element includes an airflow channel extending the longitudinal length of the airflow element and is non-parallel with the longitudinal axis. The airflow channel directs inlet air into the capsule cavity. The airflow element includes a resealable membrane configured to reseal when a piercing element is withdrawn from the resealable membrane.

In some embodiments, the distal end portion further includes a piercing element coupled to the distal end portion. The piercing element may be coupled to the distal end portion and adjacent to the distal end. The piercing element may be configured to move between a relaxed position and a piercing position. The piercing element extending through the resealable membrane and into the capsule cavity in the piercing position. The piercing element being spaced apart from the resealable membrane in the relaxed position.

In these embodiments, the distal end portion may surround a portion of the piercing element. The piercing element may move along a longitudinal axis between a piercing (activated) position and a relaxed position. A biasing element may maintain the piercing element in the relaxed position. The biasing element may be a spring member. The biasing element may compress when the piercing element is pressed into the piercing position. Releasing the piercing element allows the biasing element to force the piercing element back to the relaxed position.

The piercing element may be a rigid element capable of piercing the resealable membrane and a capsule contained within the capsule cavity. The piercing element may be a metal element such as a needle.

The one or more airflow channels through the airflow element initiates "swirling" air flow though the capsule cavity. The swirling air flow may cause a capsule contained within the capsule cavity to rotate and release pharmaceutically active particles (once pierced) into the airflow through the dry powder inhaler. Preferably there may be more than one airflow channel through the airflow element. The airflow element extends from a first lateral (orthogonal to the longitudinal axis) face to an opposing second lateral face a longitudinal length defining the distance between the first lateral face to an opposing second lateral face. The airflow channel preferably extends the total longitudinal length of the airflow element. The first lateral face may define the upstream boundary of the capsule cavity when the distal end portion is coupled to the mouthpiece portion. The airflow channel may extend from the first lateral face to the second lateral face and define a curved or arcuate path.

The airflow channel may be continuously non-parallel with the longitudinal axis of the inhaler along an entire length of the airflow channel. The airflow channel may be parallel along a portion of the length of the airflow channel and non-parallel along a remaining portion of the length of the airflow channel. The airflow channel may be parallel for a first portion or upstream portion of the airflow channel and be non-parallel for a second portion or downstream portion of the airflow channel exiting into the capsule cavity. The second portion may define a about 50% or less, or from about 5% to about 50%, or from about 10% to about 30% of the total airflow channel length.

The airflow channel may be a channel element defined along an outer surface of the airflow element and extending along a length of the airflow element. The airflow element may define three sides of the airflow channel. The airflow element may define a bottom surface and opposing depth sides that define a depth of the airflow channel. The airflow element may be inserted into the distal end portion of the inhaler body and optionally form a portion of the distal end of the inhaler body. The inhaler body may surround at least about 75%, or at least about 85% or at least about 90% or 100% of the length of the airflow element. The distal end portion of the inhaler body may contain and hold the airflow element in place within the distal end portion of the inhaler body.

The airflow element may be inserted into the distal end portion of the inhaler body and may be fixed to the inhaler body by friction fit, mechanical fit, or an adhesive, for example. A distal end portion of the inhaler body may cooperate with the airflow element airflow channel to enclose the airflow channel or form the remaining top surface of the airflow channel. The top surface may oppose the bottom surface defined by the airflow element. The top surface and bottom surface may be parallel to each other. The opposing depth sides may be parallel to each other. The opposing top surface and bottom surface may be orthogonal to the opposing depth sides.

The airflow channel may extend a distance along an arc that is co-axial with the longitudinal axis. The airflow channel may be curved with respect the longitudinal axis of the inhaler. The airflow channel may rotate around the circumference of the airflow element as a function of a location along the airflow element longitudinal length. The airflow channel may rotate around about 5% to about 100%, or about 25% to about 50% of the circumference of the airflow element. The airflow channel may rotate around the circumference of the airflow element an arc length (distance when viewing the airflow element from the first lateral face) having a central angle (that may be coincident with the longitudinal axis of the inhaler body) in a range from about or from about 5 degrees to about 360 degrees, or about 45 degrees to about 180 degrees, or from about 45 degrees to about 135 degrees.

The airflow channel may enter the capsule cavity at an angle relative to the longitudinal axis. The airflow channel may enter the capsule cavity at an angle in a range from about 5 degrees to about 89 degrees, or about 45 degrees to about 89 degrees, or about 60 degrees to about 89 degrees, or about 70 degrees to about 88 degrees. The airflow channel may have a first portion parallel with the longitudinal axis and a second portion exiting into the capsule cavity at an angle relative to the longitudinal axis as described above.

The airflow channel may include one, or two, or two or more air channels formed into the airflow element. The airflow channel may include at least two, or three or more air channels formed into the airflow element. The airflow channels may be located symmetrically about the airflow element. The airflow channels may oppose each other about the airflow element along the airflow element length. The airflow channels may be equally spaced apart from each other about the airflow element along the airflow element length. The one or more airflow channels may have a helical shape (forming a portion of a spiral). The helical air channels may be symmetrically disposed along the airflow element length and preferably oppose each other along the airflow element length. The airflow channels may each extend a distance along an arc that are each co-axial with the longitudinal axis. The inhaler body may form the top surface for each airflow channel.

The airflow element and airflow channel defined thereon may be precisely designed and manufactured to impart the desired air flow pattern through the capsule cavity of the inhaler. This distal end portion and airflow element may form a separate piece assembly that may provide for a simple and reliable manufacture and performance of the dry powder inhaler.

The airflow element may have a longitudinal length in a range from about 3 mm to about 12 mm, or from about 4 mm to about 10 mm, or from about 5 mm to about 9 mm, or about 7 mm. The airflow element may have an outer diameter sufficient to form a close or friction fit with the inner diameter of the distal end portion. The airflow element may have an outer diameter in a range from about 5 mm to about 10 mm, or from about 6 mm to about 9 mm, or about 6.5 mm to about 8.5 mm, or about 7.5 mm.

The airflow element may include a linear piercing channel extending through the length of the airflow element. The linear piercing channel may extend along a central axis of the airflow element. The linear piercing channel may be co-axial or coincident with the longitudinal axis of the inhaler body. The linear piercing channel may be sized to allow a piercing element to pass through the linear piercing channel. The linear piercing channel may have a diameter in a range from about 0.5 mm to about 2 mm.

The airflow element may include a resealable element disposed on or within or occluding the linear piercing channel. The linear piercing channel includes a first end forming a portion of the first lateral face and an opposing second end forming a portion of the second lateral face. The resealable element may be disposed on or within the first lateral face or second lateral face. The resealable element may form a portion of the first lateral face or second lateral face.

The resealable membrane may seal the linear piercing channel. The resealable membrane may form a hermetic or airtight seal or barrier along the linear piercing channel. The linear piercing channel may be formed of a pierce-able material. A piercing element may pass through the resealable membrane and puncture the capsule within the capsule cavity. The resealable membrane may reseal once the piercing element is retracted or removed from the resealable membrane.

The resealable membrane is configured to close a void created in the resealable membrane created by a piercing element such as a needle. The resealable membrane may be pierced and seal or close the void a plurality of times, such as at least about 3 three times, or at least about 5 times, or at least about 10 times or at least about 20 times. The void is created through the thickness of the resealable membrane. The resealable membrane may have a thickness in a range from about 0.1 to about 5 millimetres, or from about 0.5 to about 2 millimetres. The resealable membrane may be formed of any resilient material. Resealable membranes may include a septum-like element. Resealable membranes may be formed of elastic material such as rubber, silicone, metal foil co-laminated with a polymer, or latex and the like.

The capsule cavity may define a cylindrical space configured to contain a capsule (that may have an obround shape). The capsule cavity may have a length of about at least 110% to less than about 200% of a length of the capsule contained therein. The capsule cavity may have a substantially uniform or uniform diameter along the length of the capsule cavity. The capsule cavity may have a substantially cylindrical or cylindrical cross-section along the length of the capsule cavity. The capsule cavity may have a uniform diameter along the length of the capsule cavity that is from about 101% to about 125%, or from about 105% to about 110% of the outer diameter of the capsule contained within the capsule cavity. The configuration of the capsule cavity may allow the capsule to rotate with stability within the capsule cavity. The longitudinal axis of the capsule may rotates with stability about the longitudinal axis of the inhaler body during inhalation. The length of the capsule cavity may form an airtight barrier.

The capsule may contain pharmaceutically active particles. The capsule cavity may have a shape similar to the shape of the capsule. The capsule cavity may have a circular cross-sectional shape and a first diameter and the capsule may have a second diameter being less than the first diameter. The second diameter may be in a range from about 80% to about 99% of the first diameter, or the second diameter may be in a range from about 90% to about 98% of the first diameter. The capsule cavity may have a length of about 20 mm and an inner diameter of about 6.6 mm when containing a capsule size 3 flat. The cavity may have a length of about 24 mm and an inner diameter of about 7.7 mm when containing a capsule size 1 flat.

The capsule rotates about its longitudinal or central axis when air flows through the inhaler. The capsule may be formed of an airtight material that may be pierced or punctured by a piercing element that may be separate or combined with the inhaler. Preferably, the piercing element forms a single hole or aperture in the capsule. The capsule preferably has an obround shape. This single, singular, or only one, hole or aperture in the capsule is preferably located on a hemispherical end of the capsule. Preferably this single, singular, or only one, hole or aperture in the capsule is preferably located on a hemispherical end of the capsule at a location that is coincident with the axis of rotation of the capsule during use.

The capsule may formed of a metallic or polymeric material that serves to keep contaminates out of the capsule but be pierced or punctured by a piercing element prior to consumption of the pharmaceutical active particles within the capsule. The capsule may be formed of a polymer material. The polymer material may be hydroxypropylmethylcellulose (HPMC). The capsule may be a size 1 to size 4 capsule, or a size 3 capsule.

A consumer may access the inhaler capsule cavity to insert the capsule consumable into the inhaler capsule cavity or replace a capsule consumable with a full or un-used capsule consumable into the inhaler capsule cavity.

The dry powder inhaler includes a mouthpiece portion removably coupled to a distal end portion. The mouthpiece portion has a first mating end that fits or mates with a second mating end of the distal portion. The first mating end couples to the second mating end. The first mating portion may snap-fit to the second mating end. The first mating portion may screw onto or be in threaded engagement with the second mating end. The first mating portion may magnetically couple with the second mating end. The first mating portion may have a friction fit with the second mating end. The first mating portion may form an air tight fit or connection with the second mating end.

The capsule may be configured to rotate about its' longitudinal or central axis when inhalation air flows through the dry powder inhaler (from the distal end air inlet through the receptacle to the mouthpiece air outlet). The capsule may be formed of an airtight material that may be pierced or punctured by the piercing element of the inhaler system.

The capsule contains a dry powder comprising pharmaceutically active particles and optionally flavour particles. The capsule may contain a predetermined amount of dry powder. The capsule may contain enough dry powder to provide at least 2 inhalations or "puffs", or at least about 5 inhalations or "puffs", or at least about 10 inhalations or "puffs". The capsule may contain enough dry powder to provide from about 5 to about 35 inhalations or "puffs", or from about 8 to about 25 inhalations or "puffs". Each inhalation or "puff" releases an approximate or substantially equal or equivalent amount of dry powder into the inhalation air stream.

The capsule may contain a dry powder about 50% to about 95% by weight pharmaceutically active particles and from 50% to 5% by weight flavour particles, or from 70% to about 90% by weight pharmaceutically active particles and from 30% to 10% by weight flavour particles. The capsule may contain from 30 mg to 70 mg of dry powder, or from 40 mg to 60 mg of dry powder.

Preferably, the capsule contains nicotine particles and flavour particles. The capsule may contain a dry powder about 50% to about 95% by weight nicotine particles and from 50% to 5% by weight flavour particles, or from 70% to about 90% by weight nicotine particles and from 30% to 10% by weight flavour particles. The capsule may contain from 30 mg to 70 mg of dry powder, or from 40 mg to 60 mg of dry powder. The nicotine particles may contain from about 1% to about 10% effective nicotine, or from about 3% to about 7% effective nicotine, or about 5% effective nicotine.

When flavour particles are blended or combined with the pharmaceutically active particles within the capsule, the flavour particles are present in an amount that provides the desired flavour to each inhalation or "puff" delivered to the user.

The pharmaceutically active particles may have any useful size distribution for inhalation delivery preferentially into the lungs of a user. The capsule may include other particles than the pharmaceutically active particles. The pharmaceutically active particles and the other particles form a powder system.

The powder system may have at least about 40% or at least about 60%, or at least about 80%, by weight of the powder system comprised in pharmaceutically active particles having a particle size of about 10 micrometres or less, or 5 micrometers or less, or in a range from about 1 micrometer to about 3 micrometres.

The powder system may have at least about 40% or at least about 60%, or at least about 80%, by weight of the powder system comprised in nicotine particles having a particle size of about 10 micrometres or less, or 5 micrometers or less, or in a range from about 1 micrometer to about 3 micrometres.

The pharmaceutically active particles may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Preferably the pharmaceutically active particle are nicotine particles. Nicotine in the powder system or nicotine particles is preferably a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid is leucine such as, L-leucine. Providing an amino acid such as L-leucine with the particles comprising nicotine, may reduce adhesion forces of the particles comprising nicotine and may reduce attraction between nicotine particles and thus reduce agglomeration of nicotine particles.

Similarly, adhesion forces to particles comprising flavour is also reduced thus agglomeration of pharmaceutically active particles with flavour particles is also reduced. The powder system described herein thus may be a free-flowing material and possess a stable relative particle size of each powder component even when the pharmaceutically active particles and the flavour particles are combined.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour particles of the powder system comprised in particles having a particle size of about 20 micrometres or greater. The powder system may have at least about 40% or at least about 60%, or at least about 80%, by weight of the flavour particles of the powder system comprised in particles having a particle size of about 50 micrometres or greater. The powder system may have at least about 40% or at least about 60%, or at least about 80%, by weight of the flavour particles of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the pharmaceutically active component during consumption or inhalation thereof.

Flavourants or flavours refer to a variety of flavour materials of natural or synthetic origin. They include single compounds and mixtures. Preferably the flavour or flavourant has flavour properties that enhance the experience of the pharmaceutically active component (preferably nicotine) during consumption. Preferably, the flavour is chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like. Further suitable flavours include, horseradish oil, garlic extract, onion oil, black pepper, cayenne pepper, ginger oil, thyme oil, cinnamon bark oil, turmeric, fenugreek, cardamom, rosemary extract, grapefruit oil, andrographis extract carvacrol, thymol, monomenthyl succinate, N-(2-hydroxyethyl)-2,3-dimethyl-2-isopropyl butanamide, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature and are well-known to the person skilled in the art of flavouring, i.e. of imparting an odor or taste to a product.

The flavourant may be a high potency flavourant and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound is magnesium stearate. Providing an adhesion reducing compound such as magnesium stearate with the flavour particle, especially coating the flavour particle, reduces adhesion forces of the particles comprising flavour and may reduce attraction between flavour particles and thus reduce agglomeration of flavour particles. Thus, agglomeration of flavour particles with nicotine particles is also reduced. The powder system described herein thus may possess a stable relative particle size of the particles comprising nicotine and the particles comprising flavour even when the nicotine particles and the flavour particles are combined. The powder system preferably is free flowing.

Conventional formulations for dry powder inhalation typically contain carrier particles that serve to increase the fluidization of the active particles since the active particles may be too small to be influenced by simple airflow through an inhaler. These powder systems typically require carrier particles. These carrier particles may be a saccharide such as lactose or mannitol that have a particle size greater than about 50 micrometres. The carrier particles may be utilized to improve dose uniformity by acting as a diluent or bulking agent in a formulation. These conventional formulations typically require high speed inhalation airflows and deglomeration elements and sieve elements to achieve a particle size that will enter the pulmonary system. Inhalation airflow boosting elements, deglomeration elements, and sieve elements add complexity and cost of the dry powder inhaler.

The powder system utilized with the dry powder inhaler of the invention may be carrier-free or substantially carrier-free. Being carrier-free or substantially carrier-free may allow the dry powder and to be inhaled and the pharmaceutically active particles be delivered to the user's lungs at inhalation or airflow rates that are similar to typical smoking regime inhalation or airflow rates. Preferably any carrier-like particles are limited to the flavour particles or flavour component of the dry power system.

The dry powder system may be combined in a single capsule. As described above, the dry powder system may each have reduced adhesion forces that result in a stable powder formulation where the particle size of each component does not substantially change when combined.

The inhaler described herein are less complex and have a simplified storage and airflow path as compared to conventional dry powder inhalers. Advantageously, rotation of the capsule within the inhaler system aerosolizes the dry powder system and may assist in maintaining a free-flowing powder. Thus, this dry powder inhaler does not require the typical high inhalation rates of conventional inhalers to deliver the pharmaceutically active particles described above deep into the lungs.

The inhaler system may use a flow rate of less than about 5 L/min or less than about 3 L/min or less than about 2 L/min or about 1.6 L/min. Preferably, the flow rate is in a range from about 1 L/min to about 3 L/min or from about 1.5 L/min to about 2.5 L/min. Preferably, the inhalation rate or flow rate is similar to that of Health Canada smoking regime, that is, about 1.6 L/min.

The inhaler may be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

The dry powder utilized with the dry powder inhaler of the invention may eliminate or substantially reduce any exhalation of pharmaceutically active particles during the "exhale" phase. Preferably nearly all, or at least about 99% or at least about 95% or at least 90% of the pharmaceutically active particle has a particle size that is delivered to the lungs but are not small enough to be exhaled by tidal breathing. This pharmaceutically active particle size may be in a range from about 0.75 micrometers to about 5 micrometers, or from 0.8 micrometers to about 3 micrometers, or from 0.8 micrometers to about 2 micrometers.

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 1:
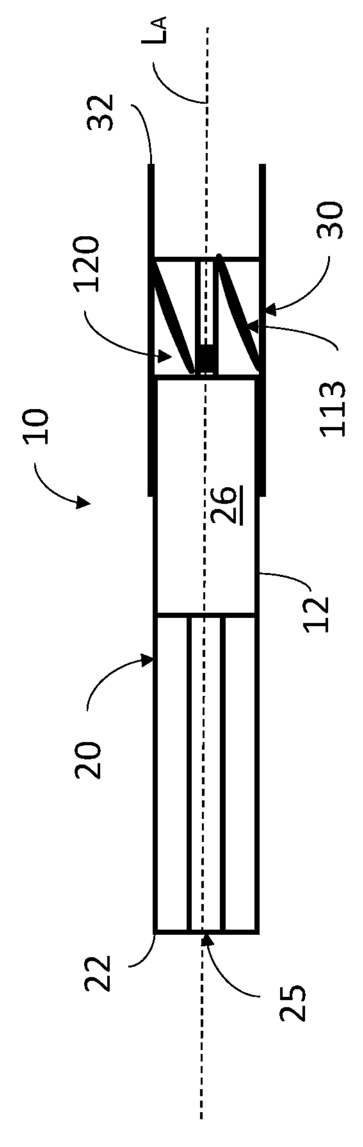
FIG. 1 is a schematic diagram of an illustrative dry powder inhaler according to the invention.
Figure 2:
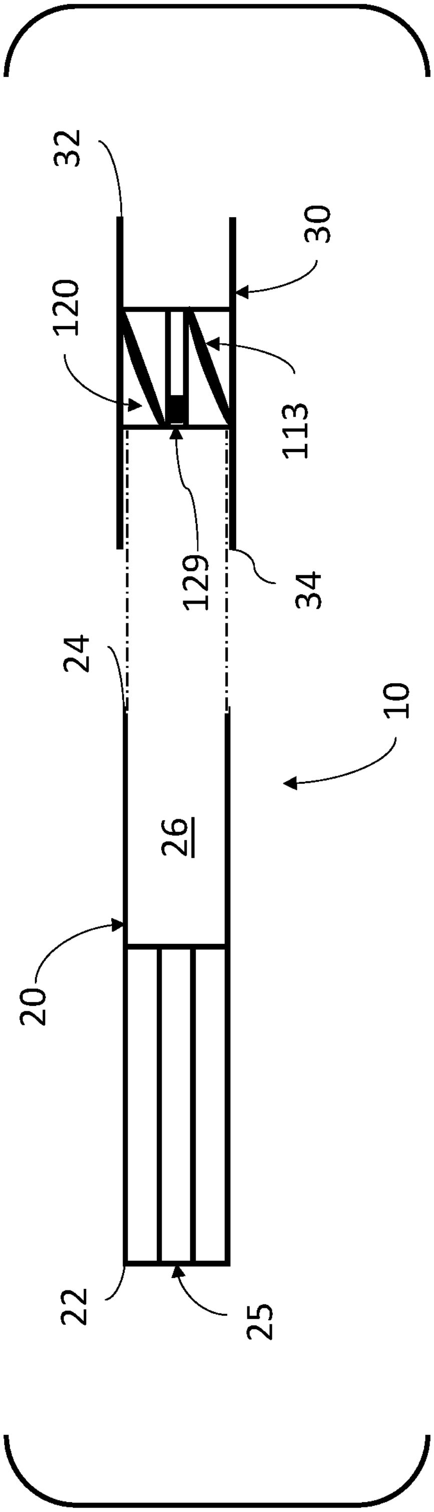
FIG. 2 is an exploded schematic view of the dry powder inhaler of FIG. 1 where the mouthpiece portion is uncoupled from the distal end portion.
Figure 3A:
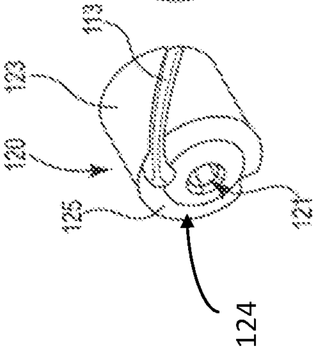
FIG. 3A and FIG. 3B are perspective views of an illustrative airflow element.
Figure 3B:
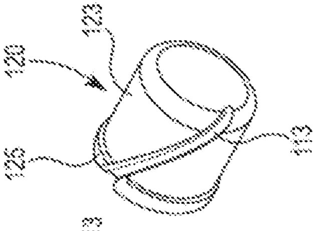

FIG. 1 is a schematic diagram of an illustrative dry powder inhaler 10 according to the invention. FIG. 2 is a schematic diagram of the illustrative inhaler system 10 of FIG. 1 with the distal end portion 30 un-coupled from the mouthpiece portion 20. Referring to FIG. 1, a dry powder inhaler 10 includes an inhaler body 12 extending from a mouthpiece end 22 to a distal end 32. The inhaler body 12 includes a mouthpiece portion 20 removably coupled to a distal end portion 30. The mouthpiece portion 20 extends between the mouthpiece end 22 and a first mating end 24. The distal end portion 30 extends between a second mating end 34 and the distal end 32.

The mouthpiece portion 20 includes a capsule cavity 26 defined within the first mating end 24 and a mouthpiece air channel 25 extending from the mouthpiece end 22 to the capsule cavity 26.

The distal end portion 30 includes an airflow element 120 disposed within the distal end portion 30 and extending a longitudinal length to the capsule cavity 26. The airflow element 120 includes an airflow channel 113 extending the longitudinal length of the airflow element 120 and is non-parallel with the longitudinal axis LA, the airflow channel 113 directs inlet air into the capsule cavity 26. The airflow element 120 includes a resealable membrane 129 configured to reseal when a piercing element is withdrawn from the resealable membrane 129.

FIG. 2 is a schematic diagram of the illustrative dry powder inhaler system 10 of FIG. 1 with the distal end portion 30 un-coupled from the mouthpiece portion 20. The distal end portion 30 may be coupled and un-coupled from the mouthpiece portion 20 with a suitable coupling means, such as, a threaded connection, a quick-connect coupling, magnetic coupling, cantilever coupling, or friction-fit coupling, for example. The first mating end 24 is complementary with the second mating end 34 and may form a generally air-tight connection.

This reusable dry powder inhaler 10 may be utilized by placing a capsule (150 see FIG. 7) into the capsule cavity 26 then mating the mouthpiece portion 20 to the distal end portion 30. Then the capsule may be pierced by inserting a piercing element through the airflow element 120 resealable membrane 129 and into the capsule in the capsule cavity 26. Then removing the piercing element from the capsule and resealable membrane 129. A user then draws air through the inhaler 10 such that the airflow element 120 airflow channels 113 produce swirling air flow to induce rotation of a capsule contained within the capsule cavity 26 and release solid particles or dry powder from the capsule to form a depleted capsule.

The depleted capsule may then be replaced with a fresh capsule by uncoupling the mouthpiece portion 20 from the distal end portion 30 and removing the depleted capsule from the capsule cavity. A fresh or new capsule may then be placed in the capsule cavity 26 and the process repeats itself.

FIG. 3A to FIG. 6 views of an illustrative airflow element 120. FIG. 3A to FIG. 4B illustrate opposing curved, or helical air channels 113 rotating about the circumference as a function of a location along the length of the airflow element 120. The airflow element 120 may include a collar element 125 having a larger diameter than the remaining body 123 of the airflow element 120.

FIG. 3A, FIG. 4A, FIG. 5 and FIG. 6 illustrate a linear piercing channel 121 extending through the length of the airflow element 120. The linear piercing channel 121 may extend along a central axis of the airflow element 120. The linear piercing channel 121 may coincide with the longitudinal axis LA of the dry powder inhaler 10. The linear piercing channel 121 may extend the entire lateral length of the airflow element 120 (while the resealable element 129 may occlude a portion of the linear piercing channel 121 length.

Figure 4A:
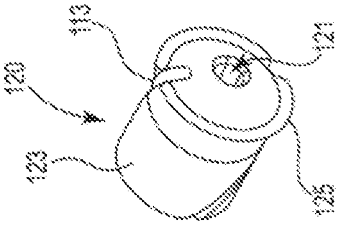
FIG. 4A and FIG. 4B are perspective views of another illustrative airflow element.
Figure 4B:
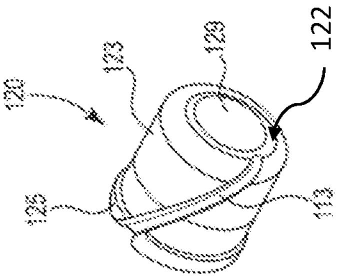
Figure 5:
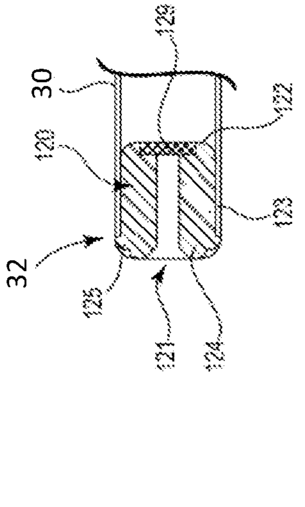
FIG. 5 is a cross-sectional schematic diagram of another illustrative airflow element.
Figure 6:
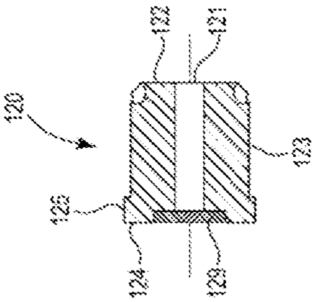
FIG. 6 is cross-sectional schematic diagram of another illustrative airflow element.

FIG. 4B, FIG. 5 and FIG. 6 illustrate a resealable element 129 disposed on or within or occluding the linear piercing channel 121. FIG. 4B and FIG. 5 illustrate a resealable element 129 disposed on the airflow element first lateral face 122 and sealing the linear piercing channel 121. FIG. 6 illustrates a resealable element 129 disposed on the airflow element second lateral face 124 and sealing the linear piercing channel 121. The resealable membrane 129 may form a portion of the first lateral face 122 or second lateral face 124.

The resealable membrane 129 may define a portion of an upstream boundary of the capsule cavity 26 when the mouthpiece portion 20 is coupled to the distal end portion 30. The resealable membrane 129 may coincide with the longitudinal axis LA of the inhaler 10.

The airflow element 120 may include two airflow channels 113 extending the longitudinal length of the airflow element 120 and is non-parallel with the longitudinal axis. The airflow channels 113 produce swirling air flow to induce rotation of a capsule contained within the capsule cavity 26. The airflow element 120 has a longitudinal length defined between a first lateral face 122 and an opposing second lateral face 124. The airflow channel 113 extends between the first lateral face 122 and the second lateral face 124.

The first lateral face 122 may define an upstream boundary of the capsule cavity 26 when the mouthpiece portion 20 is coupled to the distal end portion 30.

Figure 7:
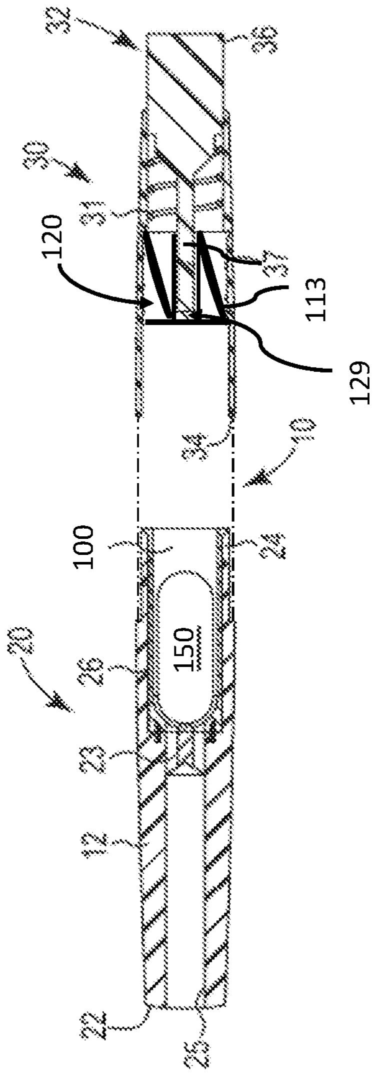
FIG. 7 is a cross-sectional view of another illustrative dry powder inhaler according to the invention.

FIG. 7 is a schematic diagram of another illustrative dry powder inhaler 10. The dry powder inhaler body 12 is illustrated with the distal end portion 30 un-coupled from the mouthpiece portion 20 and a capsule 150 within the capsule cavity 26. This illustrative dry powder inhaler 10 includes a piercing element 36 coupled to the distal end portion 30 and adjacent to the distal end 32. The piercing element 36 is configured to move between a relaxed position and a piercing position, the piercing element extending through the resealable membrane and into the capsule cavity in the piercing position, the piercing element being spaced apart from the resealable membrane in the relaxed position.

The mouthpiece portion 20 includes a capsule cavity 26 defined within the first mating end 24 and a mouthpiece air channel 25 extending from the mouthpiece end 22 to the capsule cavity 26. A capsule cavity outlet air channel 23 may provide airflow communication with the mouthpiece air channel 25 to the capsule cavity 26.

The distal end portion 30 includes an airflow element 120 disposed within the distal end portion 30 and extending a longitudinal length to the capsule cavity 26. The airflow element 120 includes an airflow channel 113 extending the longitudinal length of the airflow element 120 and is non-parallel with the longitudinal axis LA, the airflow channel 113 directs inlet air into the capsule cavity 26. The airflow element 120 includes a resealable membrane 129 configured to reseal when a piercing element is withdrawn from the resealable membrane 129.

The distal end portion 30 airflow element 120 may form the upstream boundary of the capsule cavity 26 at the first mating end 24 when the mouthpiece end 20 is coupled to the distal end 30. The piercing element 36 is configured to move between a relaxed position (FIG. 7) and a piercing position (not shown). The piercing needle 37 extends through the linear piercing channel 121 and through the resealable membrane 129 and into the capsule cavity 26 (forming a single aperture in the capsule 150) in the piercing position. The resealable membrane 129 is configured to reseal when the piercing needle 37 moves from the piercing position to the relaxed position. A biasing element 31 or spring may provide the force to return the piercing element 36 (piercing needle 37) to the relaxed position. The first mating end 24 is complementary with the second mating end 34 and may form a generally air-tight connection.

During use, inlet air enters the distal lateral face of the airflow element 120 and flows along the length of the airflow element 120 along the airflow channel exiting the opposing lateral face of the airflow element 120 in an airflow current that causes the capsule 150 to rotate within the capsule cavity 26.

The receptacle cavity 26 is configured to mate with the receptacle article 100. The detachable distal portion 30 may be removed from the mouthpiece portion 20 to expose the receptacle cavity 26 to replace the modular and used or depleted receptacle article 100 with an un-used or full receptacle article 100.

The invention claimed is:

1. A dry powder inhaler, comprising:

an inhaler body extending from a mouthpiece end to a distal end, the inhaler body comprising a mouthpiece portion removably coupled to a distal end portion, the mouthpiece portion extending between the mouthpiece end and a first mating end, the distal end portion extending between a second mating end and the distal end, the mouthpiece portion consisting of:

a capsule cavity defined within the first mating end;

a mouthpiece air channel extending from the mouthpiece end to the capsule cavity;

the distal end portion comprising:

an airflow element disposed within the distal end portion and extending a longitudinal length along a longitudinal axis to the capsule cavity, the airflow element comprises:

an airflow channel extending the longitudinal length of the airflow element and being non-parallel with the longitudinal axis, the airflow channel directs inlet air into the capsule cavity, and a resealable membrane configured to reseal when a piercing element is withdrawn from the resealable membrane wherein the distal end portion is removable from the mouthpiece portion to access the capsule cavity.

2. The dry powder inhaler according to claim 1, wherein the airflow element comprises a second airflow channel extending the longitudinal length of the airflow element and being non-parallel with the longitudinal axis, wherein the airflow channel and the second airflow channel produce swirling air flow to induce rotation of a capsule contained within the capsule cavity.

3. The dry powder inhaler according to claim 1, wherein the airflow element has an airflow longitudinal length defined between a first lateral face and an opposing second lateral face, the airflow channel extends between the first lateral face and the second lateral face.

4. The dry powder inhaler according to claim 3, wherein the resealable membrane forms a portion of the first lateral face or second lateral face.

5. The dry powder inhaler according to claim 3, wherein the first lateral face defines an upstream boundary of the capsule cavity.

6. The dry powder inhaler according to claim 1, wherein the airflow channel defines a curved or arcuate or helical path along the longitudinal length of the airflow element.

7. The dry powder inhaler according to claim 1, wherein the airflow channel is curved and rotates around a circumference of the airflow element as a function of a location along the longitudinal length of the airflow element.

8. The dry powder inhaler according to claim 1, wherein the airflow channel comprises at least two opposing helical air channels that are symmetrical and each air channel extends along the longitudinal length of the airflow element.

9. The dry powder inhaler according to claim 1, wherein the airflow element comprises a linear piercing channel extending the longitudinal length of the airflow element, and the resealable membrane occludes the linear piercing channel.

10. The dry powder inhaler according to claim 1, wherein the piercing element is coupled to the distal end portion and adjacent to the distal end, the piercing element being configured to move between a relaxed position and a piercing position, the piercing element extending through the resealable membrane and into the capsule cavity in the piercing position, the piercing element being spaced apart from the resealable membrane in the relaxed position.

11. The dry powder inhaler according to claim 1, further comprising a receptacle disposed within the capsule cavity, the receptacle being a replaceable article of the dry powder inhaler, the receptacle is configured to contain a capsule.

12. A dry powder inhaler system comprising:

the dry powder inhaler according to claim 1; and a capsule disposed within the capsule cavity of the dry powder inhaler.

13. The dry powder inhaler system according to claim 12, wherein the capsule contains solid particles comprising nicotine.

14. A method of delivering pharmaceutically active particles to the user, the method comprising:

providing the dry powder inhaler according to claim 1;

providing a capsule containing pharmaceutically active particles; and delivering pharmaceutically active particles to a user using the dry powder inhaler and the capsule.

15. The method according to claim 14, wherein, the pharmaceutically active particles comprise nicotine.

16. The dry powder inhaler according to claim 2, wherein the longitudinal length of the airflow element is defined between a first lateral face and an opposing second lateral face, the airflow channel extends between the first lateral face and the second lateral face.

17. The dry powder inhaler according to claim 4, wherein the first lateral face defines an upstream boundary of the capsule cavity.

18. The dry powder inhaler according to claim 3, wherein the airflow channel defines a curved or arcuate or helical path along the longitudinal length of the airflow element.

19. The dry powder inhaler according to claim 3, wherein the airflow channel is curved and rotates around a circumference of the airflow element as a function of a location along the longitudinal length of the airflow element.

20. The dry powder inhaler according to claim 3, wherein the airflow element comprises a linear piercing channel extending the longitudinal length of the airflow element, and the resealable membrane occludes the linear piercing channel.

* * * * *